United States Patent [19]
Jägers et al.

[11] Patent Number: 5,326,897
[45] Date of Patent: Jul. 5, 1994

[54] PROCESS FOR THE STABILIZATION OF ETHANOLIC ETHYLMAGNESIUM CARBONATE SOLUTIONS

[75] Inventors: Erhard Jägers, Bornheim; Andreas Seidel, Köln; Karen Pottkämper, Hürth, all of Fed. Rep. of Germany

[73] Assignee: Hoechst Aktiengesellschaft, Frankfurt am Main, Fed. Rep. of Germany

[21] Appl. No.: 24,528

[22] Filed: Mar. 1, 1993

[30] Foreign Application Priority Data

Mar. 12, 1992 [DE] Fed. Rep. of Germany ....... 4207883

[51] Int. Cl.$^5$ ............... C07C 69/96; C07F 3/02
[52] U.S. Cl. .................. 558/260; 558/261; 260/665 R; 423/430
[58] Field of Search ........... 260/665 R; 423/430; 558/260, 261

[56] References Cited

U.S. PATENT DOCUMENTS

| | | | |
|---|---|---|---|
| 3,277,002 | 10/1966 | Hunt et al. | 252/32.7 |
| 3,761,411 | 9/1973 | Dickey | 252/42.7 |
| 4,123,446 | 10/1978 | Sifniades et al. | 260/439 R |
| 4,318,963 | 3/1982 | Smith | 428/537 |

FOREIGN PATENT DOCUMENTS

2055886 3/1991 United Kingdom .

*Primary Examiner*—José G. Dees
*Assistant Examiner*—Porfirio Nazario-Gonzalez
*Attorney, Agent, or Firm*—Connolly & Hutz

[57] ABSTRACT

In a process for the stabilization of a solution of ethylmagnesium carbonate in ethanol, which has been prepared by the reaction of a suspension of magnesium ethylate in ethanol with carbon dioxide, 0.2 to 1.0% by weight of water, based on the ethylmagnesium carbonate solution, is added to the solution or its starting materials.

4 Claims, No Drawings

PROCESS FOR THE STABILIZATION OF ETHANOLIC ETHYLMAGNESIUM CARBONATE SOLUTIONS

The invention relates to a process for the stabilization of a solution of ethylmagnesium carbonate in ethanol, which has been prepared by the reaction of a suspension of magnesium ethylate in ethanol with carbon dioxide. Alkylmagnesium carbonates are weak bases which are used in the food sector and in particular in the field of the bulk deacidification of books, where the alkylmagnesium carbonates neutralize the sulfuric acid released in the paper; relatively small amounts are converted to magnesium hydroxide and remain in the paper as a buffer after the treatment.

Methylmagnesium carbonate in a methanolic solution has hitherto been used in most cases for this purpose. Magnesium sulfate, carbon dioxide and methanol are then formed from methylmagnesium carbonate in the neutralization process.

Now, methanol and also methylmagnesium carbonate are toxic substances which involve the danger that small amounts might remain in the book and thus give rise to problems when the book is used.

As a water-polluting substance, methanol additionally creates difficulties in the actual deacidification process.

For these reasons, the use of ethylmagnesium carbonate would be considerably more favorable. Unfortunately, however, solutions of ethylmagnesium carbonate in ethanol have the property of being unstable, even at relatively low concentrations. The ethylmagnesium carbonate crystallizes after a short time, making the solutions unusable.

It has now been found, surprisingly, that ethanolic solutions of ethylmagnesium carbonate can be stabilized by adding small amounts of water to said solutions or their starting materials. In this way, even highly viscous solutions with magnesium contents of more than 5% remain stable.

The amount of water required varies in the range of 0.2–1% by weight, preferably in the range of 0.6–0.8% by weight, based on the total solution. At lower values, the solutions are not permanently stable; at higher values, precipitation phenomena occur.

The most advantageous procedure is to add the required amount of water to the ethanol in the preparation of the ethylmagnesiumcarbonate, but it can also be added to the finished ethanolic solution.

Specifically, the process of the invention for the stabilization of a solution of ethylmagnesium carbonate in ethanol, which has been prepared by the reaction of a suspension of magnesium ethylate in ethanol with carbon dioxide, comprises adding 0.2 to 1.0% by weight, based on the ethylmagnesium carbonate solution, to the solution or its starting materials.

Furthermore, the process of the invention can optionally and preferably comprise 5 a) using ethanol with the calculated water content in the preparation of the ethylmagnesium carbonate solution;

b) adding the calculated amount of water to the suspension of magnesium ethylate in ethanol; or c) adding the calculated amount of water to the finished solution of ethylmagnesium carbonate in ethanol.

The reaction temperature can be between 0° and 50° C., preferably between 20° and 30° C.

The concentration of the ethanolic ethylmagnesium carbonate solution to be stabilized can be between 0.5 and 10% by weight, preferably between 4 and 6% by weight, based on magnesium.

Example 1 (Comparative Experiment)

337.2 g of anhydrous ethanol are placed in a 1 liter flask equipped with a stirrer, a gas inlet tube, a thermometer and a reflux condenser. 117.0 g of pulverulent magnesium ethylate are then added.

After 10 minutes, $CO_2$ gas is passed into the suspension at room temperature until saturation is reached. The reaction is slightly exothermic. The reaction is brought to completion by stirring for a further 30 minutes. The product is covered with nitrogen in a closed container. After about 24 h, the solution is composed of a crystalline mass of precipitated ethylmagnesiumn carbonate.

Example 2

3.6 g of water are added to 337.2 g of absolute ethanol in a 1 liter flask equipped with a stirrer, a gas inlet tube, a thermometer and a reflux condenser. 117.0 g of pulverulent magnesium ethylate are then added.

After 10 minutes, $CO_2$ gas is passed into the suspension at room temperature until saturation is reached. The reaction is slightly exothermic. The reaction is brought to completion by stirring for a further 30 minutes. The product is covered with nitrogen in a closed container. Even after several weeks, the solution prepared in this way is still clear and free from precipitated crystalline products.

Example 3

337.2 g of anhydrous ethanol are placed in a 1 liter flask equipped with a stirrer, a gas inlet tube, a thermometer and a reflux condenser. 117.0 g of pulverulent magnesium ethylate are then added.

After 10 minutes, $CO_2$ gas is passed into the suspension at room temperature until saturation is reached. The reaction is slightly exothermic. The reaction is brought to completion by stirring for a further 30 minutes. 3.6 g of water are then added to the solution. The product is covered with nitrogen in a closed container. Even after several weeks, the solution prepared in this way is still clear and free from precipitated crystalline products.

We claim:

1. A process for the stabilization of a solution of ethylmagnesium carbonate in ethanol, which has been prepared by the reaction of a suspension of magnesium ethylate in ethanol with carbon dioxide, which comprises adding 0.2 to 1.0 % by weight o f water, based on the ethylmagnesium carbonate solution, to the solution or its starting materials.

2. The process as claimed in claim 1, wherein ethanol with the calculated water content is used in the preparation of the ethylmagnesium carbonate solution.

3. The process as claimed in claim 1, wherein the calculated amount of water is added to the suspension of magnesium ethylate in ethanol.

4. The process as claimed in claim 1, wherein the calculated amount of water is added to the finished ethylmagnesium carbonate solution.

* * * * *